(12) United States Patent
Loiacono et al.

(10) Patent No.: US 11,610,668 B2
(45) Date of Patent: Mar. 21, 2023

(54) SYSTEMS AND METHODS FOR CENTRALIZED BUFFERING AND INTERACTIVE ROUTING OF ELECTRONIC DATA MESSAGES OVER A COMPUTER NETWORK

(71) Applicant: Truveris, Inc., New York, NY (US)

(72) Inventors: Anthony J. Loiacono, Bayonne, NJ (US); Bertrand Janin, West Orange, NJ (US); Sunil Parekh, New York, NY (US)

(73) Assignee: Truveris, Inc., New York, NY (US)

( * ) Notice: Subject to any disclaimer, the term of this patent is extended or adjusted under 35 U.S.C. 154(b) by 296 days.

(21) Appl. No.: 15/703,844

(22) Filed: Sep. 13, 2017

(65) Prior Publication Data

US 2018/0075215 A1 Mar. 15, 2018

Related U.S. Application Data

(60) Provisional application No. 62/395,697, filed on Sep. 16, 2016, provisional application No. 62/395,040, filed on Sep. 15, 2016.

(51) Int. Cl.
*G16H 20/10* (2018.01)
*G16H 40/20* (2018.01)
(Continued)

(52) U.S. Cl.
CPC .............. *G16H 40/20* (2018.01); *G06Q 50/22* (2013.01); *G16H 20/10* (2018.01); *H04W 4/023* (2013.01); *H04W 4/60* (2018.02)

(58) Field of Classification Search
CPC .... G06F 19/3462; G16H 40/20; G16H 20/10; H04W 4/60; H04W 4/023; G06Q 50/22
See application file for complete search history.

(56) References Cited

U.S. PATENT DOCUMENTS 8,036,913 B1 * 10/2011 Pinsonneault ........ G06F 19/328
705/2
8,712,797 B1 * 4/2014 Bezdek .................. G06Q 30/06
705/2
(Continued)

*Primary Examiner* — Michael Tomaszewski
*Assistant Examiner* — Mohmad Muqueeth
(74) *Attorney, Agent, or Firm* — Sheppard, Mullin, Richter & Hampton LLP

(57) ABSTRACT

An electronic prescription is obtained over a network. A synthetic prescription is generated from the electronic prescription and provided to an insurance switching system. Insurance information of a patient is received from the insurance switching system based on the synthetic prescription. An auto-reversal of the synthetic prescription with the insurance switching system is triggered. A patient payment amount associated with the particular pharmaceutical is determined based on the insurance information. One or more pharmacies to fulfill the electronic prescription are identified based on patient information. An interactive routing request data message is provided to the patient, the data message including the patient payment amount and a request for selection of a particular pharmacy of the one or more pharmacies. The selection of the particular pharmacy is received from a computing device associated with the patient. In response to receiving the selection, the electronic prescription is routed to the particular pharmacy.

19 Claims, 10 Drawing Sheets

(51) Int. Cl.
*H04W 4/02* (2018.01)
*G06Q 50/22* (2018.01)
*H04W 4/60* (2018.01)

(56) References Cited

U.S. PATENT DOCUMENTS

| | | | |
|---|---|---|---|
| 2004/0078237 A1* | 4/2004 | Kaafarani | G06F 19/3456 705/2 |
| 2005/0049497 A1* | 3/2005 | Krishnan | G16H 50/20 600/437 |
| 2015/0025908 A1* | 1/2015 | Lakshminarayan | G16H 10/60 705/3 |
| 2018/0240539 A1* | 8/2018 | Doherty | G06Q 50/22 |

* cited by examiner

SYSTEMS AND METHODS FOR CENTRALIZED BUFFERING AND INTERACTIVE ROUTING OF ELECTRONIC DATA MESSAGES OVER A COMPUTER NETWORK

CROSS-REFERENCE TO RELATED APPLICATIONS

The present application claims the benefit of U.S. Provisional Patent Application Ser. No. 62/395,040, filed Sep. 15, 2016 and entitled "Computer System and Method for Managing Electronic Prescriptions," and U.S. Provisional Patent Application Ser. No. 62/395,697, filed Sep. 16, 2016 and entitled "System and Method for Patient Coordination of Prescriptions Benefits," which are hereby incorporated by reference herein.

TECHNICAL FIELD

This disclosure pertains to systems for routing electronic data messages over a computer network. More specifically, this disclosure pertains to systems for centralized buffering and interactive routing of electronic data messages over a computer network.

BACKGROUND

Under conventional approaches, patients have limited visibility into the routing of electronic prescriptions. In many instances, when choosing a pharmacy to fulfill an electronic prescription, patients are confused about their options (e.g., physical pharmacies, mail-order pharmacies, discounts and promotions, specific pharmacy locations, and/or the like), and/or do not have time to consider their options prior to authorizing a provider (e.g., physician or other healthcare professional) to select a pharmacy to receive the electronic prescription.

SUMMARY

A claimed solution rooted in computer technology overcomes problems specifically arising in the realm of computer technology. In various embodiments, an interactive routing server system is provided for buffering and interactively routing electronic data messages (e.g., electronic prescriptions) over a computer network. In some embodiments, the interactive routing server system obtains an electronic prescription (e.g., from a provider system). The computing system may store (e.g., "buffer") the electronic prescription for a limited amount of time, and may notify a patient of different pharmacies that may be capable of fulfilling the electronic prescription. The interactive routing server system may provide the patients with a list (or, other structure) of the different pharmacies, and the patient may be presented (e.g., via the patient's mobile device) with the different pharmacies. The patient may select a particular pharmacy to fulfill the electronic prescription, and the selection may be provided to the interactive routing server system. The interactive routing server system may receive the selection from the patient, and may then route the electronic prescription to the patient-selected pharmacy.

In some embodiments, the interactive routing server system determines patient payment amounts for filling electronic prescription (e.g., cash-pay amounts, co-pay amounts, discount payment amounts), and identifies potential pharmacies to fill the electronic prescription based on the patient payment amounts and/or other parameters (e.g., geographic location of a pharmacy and/or patient, pharmacy inventory, and/or the like).

In some embodiments, the interactive routing server system processes prescription query requests. For example, prior to obtaining an electronic prescription, a patient may input insurance information and pharmaceutical information for a particular pharmaceutical through an interface displayed on their mobile device, and the mobile device may formulate and provide a prescription query request to the interactive routing server system. The interactive routing server system may determine a patient payment amount for the particular pharmaceutical, and provide the patient payment amount to the patient for review. This may, for example, help the patient determine which medication to obtain prior to a provider creating an electronic prescription.

Various embodiments of the present disclosure include systems, methods, and non-transitory computer readable media configured to obtain an electronic prescription over a communication network, the electronic prescription being associated with a patient and identifying a particular pharmaceutical. A synthetic prescription is generated from the electronic prescription. The synthetic prescription is provided to an insurance switching system. Insurance information of the patient is received from the insurance switching system based on the synthetic prescription. An auto-reversal of the synthetic prescription with the insurance switching system is triggered. A patient payment amount associated with the particular pharmaceutical is determined based on the insurance information. One or more pharmacies to fulfill the electronic prescription are identified based on patient information of the patient. An interactive routing request data message is provided to the patient, the data message including the patient payment amount associated with the particular pharmaceutical and a request for selection of a particular pharmacy of the one or more pharmacies by the patient. The selection of the particular pharmacy of the one or more pharmacies is received from a computing device associated with the patient. In response to receiving the selection from the computing device associated with the patient, the electronic prescription is routed to the particular pharmacy of the one or more pharmacies.

In some embodiments, the synthetic prescription includes a patient insurance identifier associated with the patient, and an identifier of the particular pharmaceutical, the synthetic prescription capable of being processed by the insurance switching system as if it were an actual request to fulfill the electronic prescription.

In some embodiments, the insurance information of the patient includes whether the patient has insurance coverage, and if the patient has insurance coverage, insurance coverage information.

In some embodiments, the patient payment amount includes any of a deductible amount, co-pay amount, cash-pay amount, and promotion discount amount.

In some embodiments, the patient information includes a patient identifier and any of a predetermined geographic location of the patient, a current geographic location of the patient, and one or more predetermined pharmacy selection rules.

In some embodiments, the identifying, by the interactive routing server system, the one or more pharmacies to fulfill the electronic prescription based on the patient information of the patient comprises identifying, by the interactive routing server system, the one or more pharmacies to fulfill the electronic prescription based on the patient information of the patient and based on the patient payment amount.

In some embodiments, the systems, methods, and non-transitory computer readable media are further configured to gather pharmacy information from a plurality of pharmacies, the pharmacy information including any pharmaceutical inventory information, pharmaceutical pricing information, and pharmaceutical promotion information. In related embodiments, the one or more pharmacies are identified to fulfill the electronic prescription is further based on the pharmacy information.

In some embodiments, the electronic prescription is obtained from a provider system associated with the provider prescribing the electronic prescription, the interactive routing server system obtaining the electronic prescription as if the interactive routing server system comprised an actual pharmacy.

In some embodiments, the systems, methods, and non-transitory computer readable media are further configured to provide a fulfillment notification the computing device associated with the patient in response to fulfillment of the electronic prescription by the particular pharmacy of the one or more pharmacies.

These and other features of the systems, methods, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

DETAILED DESCRIPTION

Figure 1:
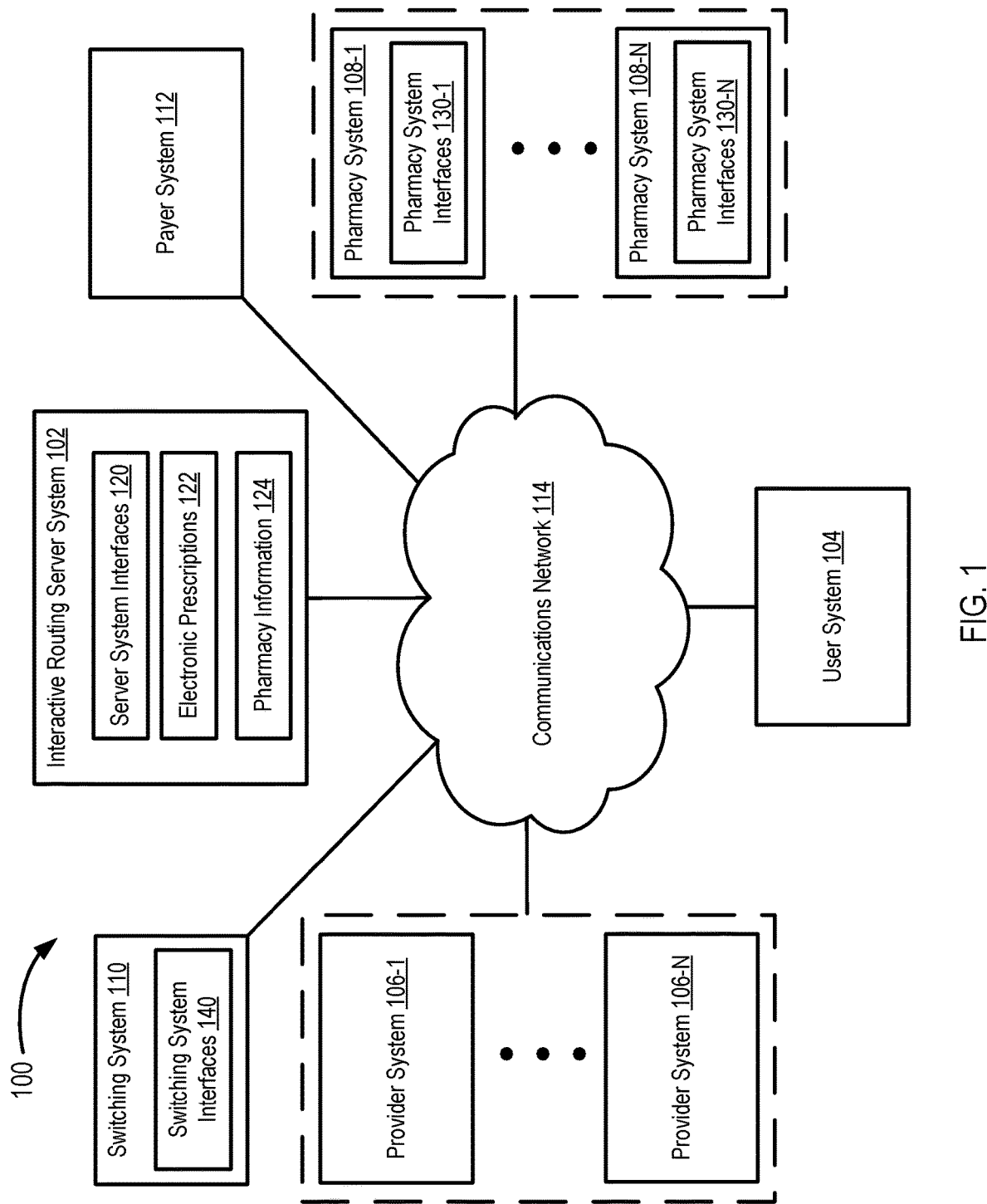
FIG. 1 depicts a diagram of an example system for centralized buffering and interactive routing of electronic data messages over a computer network according to some embodiments.

Under convention approaches, patients have limited visibility into the routing of electronic prescriptions. Typically, an electronic prescription is prepared on a computer by a provider (e.g., medical or other healthcare professional), and the provider selects a pharmacy to fulfill the prescription at the same time they are preparing the electronic prescription (e.g., while the patient is at the provider's office). In many instances, when choosing a pharmacy to fulfill the electronic prescription, patients are confused about their options (e.g., physical pharmacies, mail-order pharmacies, discounts and promotions, specific pharmacy locations, and/or the like), and/or do not have time to consider their options prior to authorizing the provider to select the pharmacy to receive the electronic prescription. Accordingly, patients often make quick and/or uninformed decisions at their provider's offices about where to send an electronic prescription without considering when the electronic prescription will be available for pickup, whether the pharmacy has the inventory necessary to fill the electronic prescription, the cost or available savings associated with the prescription and/or particular pharmacy, and/or the like. As follows, patient's often find that they need to fill the electronic prescription at a different pharmacy (e.g., because the pharmacy lacks the necessary inventory, the location of the pharmacy is no longer convenient), and need to have their provider generate a new electronic prescription, which can then be sent to the different pharmacy.

A claimed solution rooted in computer technology overcomes problems specifically arising in the realm of computer technology. In various embodiments, an interactive routing server system is provided for buffering and interactively routing electronic data messages (e.g., electronic prescriptions) over a computer network. In some embodiments, the interactive routing server system obtains an electronic prescription (e.g., from a provider system). The computing system may store (e.g., "buffer") the electronic prescription for a limited amount of time, and may notify a patient of different pharmacies that may be capable of fulfilling the electronic prescription. The interactive routing server system may provide the patients with a list (or, other structure) of the different pharmacies, and the patient may be presented (e.g., via the patient's mobile device) with the different pharmacies. The patient may select a particular pharmacy to fulfill the electronic prescription, and the selection may be provided to the interactive routing server system. The interactive routing server system may receive the selection from the patient, and may then route the electronic prescription to the patient-selected pharmacy.

In some embodiments, the interactive routing server system determines patient payment amounts for filling electronic prescription (e.g., cash-pay amounts, co-pay amounts, discount payment amounts), and identifies potential pharmacies to fill the electronic prescription based on the patient payment amounts and/or other parameters (e.g., geographic location of a pharmacy and/or patient, pharmacy inventory, and/or the like).

In some embodiments, the interactive routing server system processes prescription query requests. For example, prior to obtaining an electronic prescription, a patient may input insurance information and pharmaceutical information for a particular pharmaceutical through an interface displayed on their mobile device, and the mobile device may formulate and provide a prescription query request to the interactive routing server system. The interactive routing server system may determine a patient payment amount for the particular pharmaceutical, and provide the patient payment amount to the patient for review. This may, for example, help the patient determine which medication to obtain prior to a provider creating an electronic prescription.

FIG. 1 depicts a diagram 100 of an example system for centralized buffering and interactive routing of electronic data messages over a computer network according to some embodiments. In the example of FIG. 1, the system includes an interactive routing server system 102, a user system 104, provider systems 106-1 to 106-N (individually, the provider system 106, collectively, the provider systems 106), pharmacy systems 108-1 to 108-N (individually, the pharmacy system 108, collectively, the pharmacy systems 108), a switching system 110, a payer system 112, and a communication network 114.

The interactive routing server system 102 may function to obtain, store, and/or interactively route electronic prescriptions 122. The functionality of the interactive routing server system 102 may be performed by one or more servers (e.g., a cloud-based server) and/or other computing devices. In some embodiments, the interactive routing server system 102 functions to obtain electronic prescriptions 122 from a provider system 106 (discussed further herein) and/or other third-party system (e.g., a third-party electronic prescribing service). For example, the interactive routing server system 102 may receive an electronic prescription 122, and temporarily store (or, "buffer") the electronic prescription 122. This may allow the interactive routing server system 102 to interactively route the electronic prescription to an appropriate pharmacy system 108 (discussed further herein) based on one or more interactions with the patient associated with the electronic prescription 122.

In some embodiments, the interactive routing server system 102 functions to gather information from one or more remote systems in real-time and/or otherwise (e.g., periodically, according to a schedule, or in response to particular events). For example, the interactive routing server system 102 may gather pharmacy information 124 (e.g., pharmacy inventory, pharmacy pricing) and/or other information (e.g., insurance information). In some embodiments, the interactive routing server system 102 may utilize one or more server system interfaces 120 to gather information and/or otherwise interact with one or more remote systems. For example, the interactive routing server system 102 may utilize server system interfaces 120 to cooperate with pharmacy system interfaces 130 to gather pharmacy information from pharmacy systems 108, and/or utilize server system interfaces 120 to cooperate with switching system interfaces 140 to obtain insurance information from switching system 110 and/or payer system 112. The interfaces described herein may include application programming interfaces (APIs), software development kits (SDKs), source code, machine code, and/or server stubs.

In some embodiments, the interactive routing server system 102 functions to provide notifications (e.g., to a patient's mobile device and/or other user system) to facilitate interactive routing of electronic prescriptions 122, and/or provide updates regarding the status of electronic prescriptions 122. The notifications may be alone and/or in combination with other messages. The notifications may request additional patient information, provide insurance information, suggest pharmacies for fulfillment of prescriptions (e.g., based on prescription cost savings and geographical locations for fulfillment and dispensation of the prescription), provide drug alerts (e.g. adverse effects, toxicity, etc.), and/or provide health plan information (or, "insurance information"). Health plan information may include, for example, benefit approval, deductible amounts, co-pay amounts, restrictions (e.g., prior authorization, step therapy) and/or the like.

In some embodiments, the interactive routing server system 102 queries a patient and/or associated systems for selection of a pharmacy, and the interactive routing server system 102 routes the electronic prescription 122 to the selected pharmacy. The interactive routing server system 102 may provide a set of suitable pharmacies from which the patient may select a particular pharmacy to fulfill the electronic prescription 122. The interactive routing server system 102 may select the set of suitable pharmacies based on one or more factors, such as a patient's geographical location, previous pharmacies used by the patient, mail-order or retail-pharmacy preferences, prescription cost saving discounts, and/or the like.

In some embodiments, the interactive routing server system 102 determines prescription prices at several pharmacies in the patient's geographical location, and determines available cost saving discounts, and provides prescription costs (or, "patient payment amounts") at various pharmacies for the patient to select. The fulfilled prescription may be obtained by personal retrieval if the electronic prescription 122 was routed to a retail pharmacy system 108, or the electronic prescription 122 may be mailed to the patient if it was routed to a mail-order pharmacy system 108. Depending upon a patient's dosage of drug, frequency of dosage, long term use, available discounts, insurance co-pay, and/or the like, the interactive routing server system 102 may provide mail-order pharmacies and available prices versus retail pharmacies and prices for a patient to consider selection.

In some embodiments, the interactive routing server system 102 obtains insurance information for a patient. For example, the interactive routing server system 102 may transmit a request (e.g., utilizing a pharmacy National Provider Identifier and/or physician National Provider Identifier) to a switching system 110. As used herein, such a request may be referred to as a synthetic prescription. In order to determine a patient's coverage, the switching system 110 may contact a payer system 112 (e.g., the patient's insurance carrier or Pharmacy Benefit Manager of the plan), as though the request was an actual request to fill an electronic prescription 122, and returns the coverage information to the interactive routing server system 102. Thereafter, the interactive routing server system 102 may determine if the patient has coverage for the medication prescribed, and if the patient does have coverage, the amount of coverage therefor. The interactive routing server system 102 may then auto-reverse (e.g., cancel) the prescription with the switching system 110 and/or payer system 112, and perform an analysis to determine the availability and/or eligibility of discount cards and/or brand-name drug coupons (e.g., in the patient's geographical location and/or mail-order). After determining if discounts may be available, the interactive routing server system 102 may assess each prescription payment option to determine the most economical form of payment (e.g., insurance or cash), and may provide the information to the patient for review and selection of pharmacy and/or form of payment.

In some situations, a medication may not be covered by the formulary of the patient's plan, or there may be a generic substitute for the prescribed brand-name drug. Sometimes, the patient may not be eligible to receive coverage for a particular medication (e.g., because of prior authorization, step therapy, and/or "quantity limited" insurance restrictions). In such situations, out-of-pocket co-pay for a patient using insurance, even with a manufacturer's brand-name drug coupon applied to discount the prescription cost, may be substantially high due to limited formulary coverage, co-insurance (e.g., co-pay), and/or enrollment in high deductible prescription benefit plans. In some instances, it may be more cost effective for a patient to forgo insurance coverage and opt to utilize a discount card provided by a Pharmacy Benefit Manager and/or pharmacy.

In some embodiments, the interactive routing server system 102 may function to analyze a patient's options of utilizing insurance or paying cash. By utilizing insurance, patients may make a co-payment of cash (e.g., payment of cost of prescription not covered by insurance) and a manufacturer's coupon may be available if the prescription prescribes a brand-name drug. However, discount cards may be available to uninsured patients and those willing to pay cash (e.g., forgo insurance) if that reduces an out-of-pocket cash amount of payment price for a prescription. The interactive routing server system 102 may receive insurance parameters (e.g., from the patient), prescription parameters and/or personal information in order to obtain insurance information. The insurance parameters may include BIN, PCN, Member ID, Group No, Person Code, and/or Relationship to Policyholder. The prescription parameters include name of drug (National Drug Code (NDC)), formulation, dosage, and/or quantity. The personal information may include name, address, and/or zip code. Thereafter, the interactive routing server system 102 may retrieve the patient's insurance coverage information from the switching system 110 in communication with the payer system 112 to determine the patients' insurance eligibility and coverage within the patient's insurance plan. In some embodiments, utilizing zip code information, a plurality of retail pharmacies located in the patient's geographical location may be assessed to determine if discount cards and manufacturer's coupons may be available for the prescribed drug. The interactive routing server system 102 may search third party databases and internal databases for the discount instruments.

The user system 104 may function to facilitate interactive routing of electronic prescriptions 122. The user system 104 may be associated with a respective patient. In various embodiments, functionality of the user system 104 may be performed by one or more desktop computers, laptop computers, servers, mobile devices (e.g., smartphone, tablet) and/or other computing devices. The user system 104 may be implemented by a cloud-computing platform (e.g., a web-based portal).

In some embodiments, the user system 104 may function to present a set of pharmacies that may be capable of fulfilling an electronic prescription for a patient associated with the user system 104. For example, the user system 104 may provide a graphical user interface for displaying the set of pharmacies and receiving a patient-selection of a particular pharmacy to fulfill the electronic prescription 122.

The provider systems 106 may function to facilitate creation of electronic prescriptions 122 and/or provide electronic prescriptions 122 to remote systems (e.g., interactive routing server system 102). In various embodiments, functionality of the provider systems 106 may be performed by one or more desktop computers, laptop computers, servers, mobile devices (e.g., smartphone, tablet) and/or other computing devices. The provider systems 106 may be implemented by a cloud-computing platform (e.g., a web-based portal).

The pharmacy systems 108 may function to receive and/or fulfill electronic prescriptions 122. In some embodiments, functionality of the pharmacy systems 108 may be performed by one or more desktop computers, laptop computers, servers, mobile devices (e.g., smartphone, tablet) and/or other computing devices. The pharmacy systems 108 may be associated with retail pharmacies (or, "brick-and-mortar" pharmacies) and/or mail-order pharmacies.

The communications network 114 may represent one or more computer networks (e.g., LAN, WAN, or the like) or other transmission mediums. The communication network 114 may provide communication between systems 102-112 and/or other systems described herein. In some embodiments, the communication network 114 includes one or more computing devices, routers, cables, buses, and/or other network topologies (e.g., mesh, and the like). In some embodiments, the communication network 114 may be wired and/or wireless. In various embodiments, the communication network 114 may include the Internet, one or more wide area networks (WANs) or local area networks (LANs), one or more networks that may be public, private, IP-based, non-IP based, and so forth.

Figure 2:
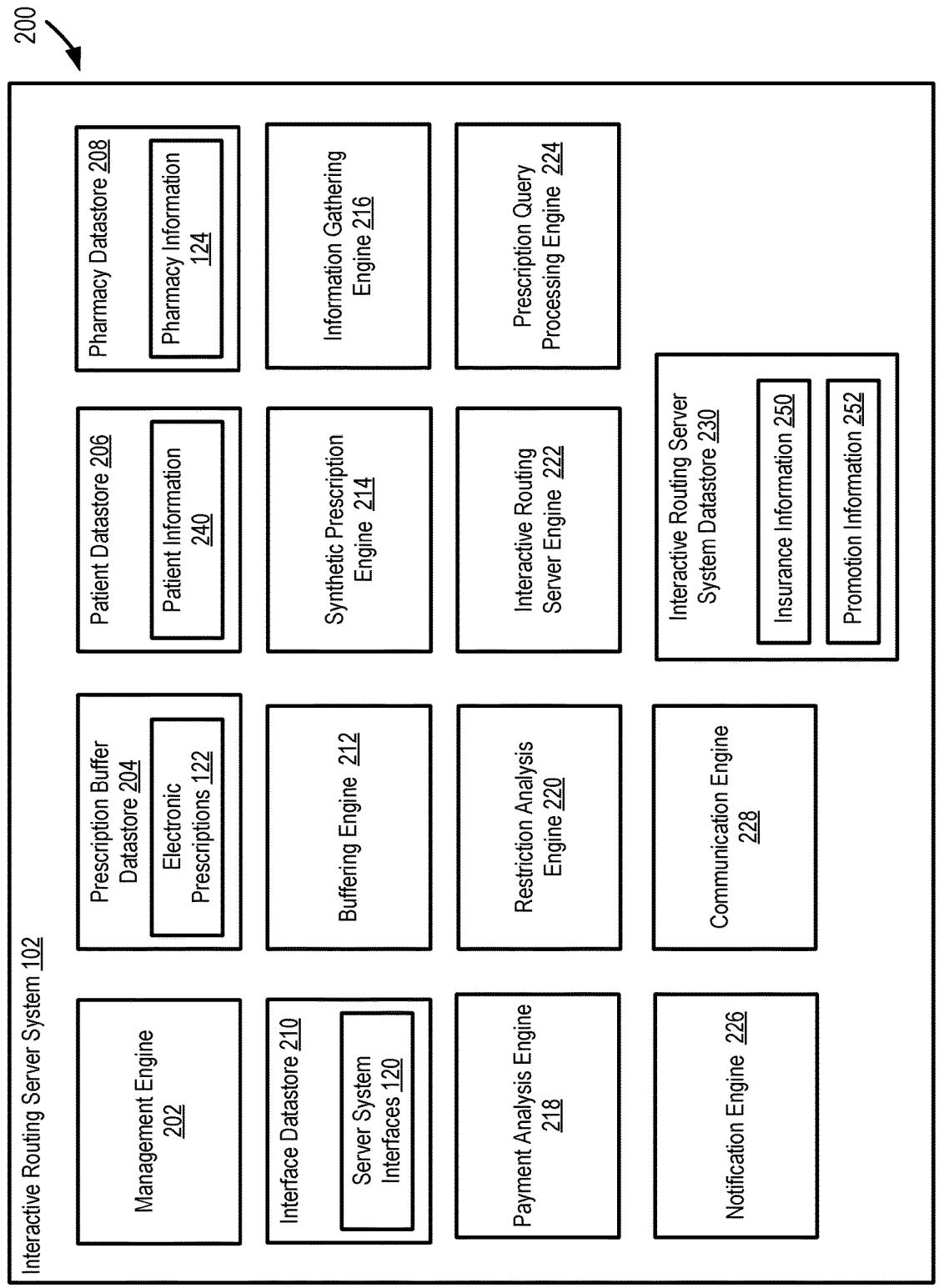
FIG. 2 depicts a diagram of an example of an interactive routing server system according to some embodiments.

FIG. 2 depicts a diagram 200 of an example of an interactive routing server system 102 according to some embodiments. In the example of FIG. 2, the interactive routing server system 102 includes a management engine 202, a prescription buffer datastore 204, a patient datastore 206, a pharmacy datastore 208, an interface datastore 210, a buffering engine 212, a synthetic prescription engine 214, an information gathering engine 216, a payment analysis engine 218, a restriction analysis engine 220, an interactive routing engine 222, a prescription query processing engine 224, a notification engine 226, a communication engine 228, and an interactive routing server system datastore 230.

The management engine 202 may be configured to manage (e.g., create, read, update, delete, or otherwise access) electronic prescriptions 122 stored in the prescription buffer datastore 204, patient information 240 stored in the patient datastore 206, pharmacy information 124 stored in the pharmacy datastore 208, server system interfaces 120 stored in the interface datastore 210, and/or other information stored in the interactive routing server system datastore 230. The management engine 202 may perform any of these operations manually (e.g., by a user interacting with a GUI) and/or automatically (e.g., triggered by one or more of the engines 212-228, discussed below). In some embodiments, the management engine 202 comprises a library of executable instructions, which are executable by one or more processors for performing any of the aforementioned management operations.

The electronic prescriptions 122 may include a variety of data related to electronic prescriptions. In some embodiments, the electronic prescriptions 122 may include some or all of the following:

Electronic Prescription Identifier: identifies the electronic prescription.

Provider Identifier: identifies the provider that prescribed the electronic prescription.

Patient Identifier: identifies the patient for whom the electronic prescription was prescribed.

Pharmaceutical Identifier: identifies one or more prescribed pharmaceuticals (or, "medications").

Pharmaceutical Dosage: prescribed dosage for the one or more prescribed pharmaceuticals.

Directions: Duration and/or other directions for taking the prescribed medication (e.g., take 1 pill up to four times per day for 10 days).

Restrictions: one or more restrictions (e.g., prior authorization, step therapy, quantity limited) associated with the electronic prescription. Restrictions may be entered during creation of the electronic prescription (e.g., by the provider) and/or subsequently associated with the electronic prescription. For example, the provider may restrict the prescription to a brand-name pharmaceutical. In another example, restrictions may be identified based on information provided by a switching system and/or payer system (e.g., particular pharmaceutical requires pre-authorization for brand name).

The patient information 240 may include a variety of data related to patients. In some embodiments, the patient information 240 may include some or all of the following:

Patient Identifier: identifies the patient.

Patient Personal Information: identifies personal information of the patient (e.g., name, address, and/or zip code).

Patient Contact Information: contact information that may be used to associate a patient with one or more user systems and/or devices (e.g., phone number, email address, fax number, URI). Contact information may be used to receive notifications.

Insurance Information: patient insurance information. This may be provided by the patient and/or obtained by the interactive routing server system 102, as discussed elsewhere herein.

Pharmacy Selections Rules: one or more rules governing selection of suitable pharmacies to present to the patient for selection of a particular pharmacy to fulfill an electronic prescription. For example, the rules may indicate preferences for various parameters, such as geographic location, mail-order or retail-pharmacies, and/or the like. Parameters may be weighted based on patient preference.

Prescription Status: a status of routed electronic prescription. For example, status may indicate that a pharmacy has received the prescription, a pharmacy has filled the prescription, the prescription has a restriction that is awaiting resolution, and/or the like.

The pharmacy information 124 may include a variety of data related to pharmacies and/or related systems. Pharmacy information 124 may be stored in one or more local datastores. In some embodiments, the pharmacy information 124 may include some or all of the following:

Pharmacy Identifier: identifies the pharmacy and/or associated pharmacy system.

Pharmacy Type: identifies whether the pharmacy is a mail-order pharmacy or a retail pharmacy.

Pharmacy Location: identifies a geolocation of the pharmacy.

Pharmacy Contact Information: contact information for the pharmacy (e.g., phone number, email address, fax number, URI).

Pharmacy Inventory Information: identifies current and/or historical pharmaceutical inventory.

Pharmacy Pricing Information: identifies current and/or historical pharmaceutical pricing.

Pharmacy Promotion Information: identifies current and/or historical promotions.

The insurance information 250 may include a variety of data related to payers. In some embodiments, the insurance information 250 may include some or all of the following:

Insurance Information Identifier: identifies the insurance information.

Patient Identifier: identifies the patient associated with the insurance information.

Payer: identifies a payer (e.g., insurance carrier or Pharmacy Benefit Manager) associated with the insurance information.

Co-Pay Amount(s): identifies co-pay amounts for one or more medications.

Cash-Pay Amount(s): identifies cash-pay amounts for one or more medications.

Promotion(s): identifies one or more promotions and/or associated promotion values.

Restrictions: one or more associated restrictions.

The promotion information 252 may include a variety of data related to promotions. In some embodiments, the promotion information 252 may include some or all of the following:

Promotion Information Identifier: identifies the promotion information.

Promotion Type: type of promotion (e.g., co-pay promotion, co-insurance promotion, deductible promotion).

Manufacturer Information: information of the manufacturer providing the promotion information. For example, bank identifier number (BIN), process control number (PCN), group number, and/or the like.

Promotion Parameters: information used to determine eligibility for, and/or otherwise process, one or more promotions. For example, pharmaceutical identifier (e.g., medication name), dosage, promotion value (e.g., 10% discount), reimbursement rules (e.g., pharmacy offset patient cost and manufacturer reimburse pharmacy), eligible insurance carriers, eligible patients (e.g., identified by member identifiers), dates of promotion (e.g., indicating when promotion is active), and/or the like.

In some embodiments, promotion information 252 is provided by one or more remote systems (e.g., a pharmaceutical manufacturer system, a pharmacy systems, and/or the like). In some embodiments, promotion information 252 is automatically provided by pharmacy systems. For example, a user (e.g., pharmacy technician) can input information regarding a patient's prescription and/or insurance information in a pharmacy system. The pharmacy system can store pre-defined promotion information regarding the particular co-pay promotion associated with the pharmacy system (e.g., the manufacturer's promotion BIN, PCN, and/or group number) such that the user need not input this promotion information manually. In turn, the automatically provided promotion information 252 can be provided to the interactive routing server system 102 alongside patient information and/or prescription information.

In some embodiments, promotion information 252 is automatically obtained by the interactive routing server system 102. For example, the interactive routing server system 102 may generate a promotion request including information regarding a particular patient and prescription in response to receiving an electronic prescription 122 and/or other trigger event. The interactive routing server system 102 can provide the promotion request to pharmacy systems, manufacturer systems, and/or other associated promotion entities, and based on the response, determine if a promotion exists, if the patient is eligible, and determine the payment to be provided to reduce the patient's expenses.

The buffering engine 212 may function to store electronic prescriptions 122. The electronic prescriptions 122 may be stored in the prescription buffer datastore 204. In some embodiments, the buffering engine 212 may store some or all electronic prescriptions 122 for a limited amount of time. For example, the limited amount of time may be predetermined and/or based on one or more conditions. The conditions may include storing the electronic prescriptions 122 until they are routed and/or received by a pharmacy. In some embodiments, the electronic prescriptions 122 may expire (e.g., after the limited amount of time has elapsed). In some embodiments, the buffering engine 212 may store electronic prescriptions 122 persistently in addition to for a limited amount of time. This may help, for example, facilitate audits and/or historical searches.

The synthetic prescription engine 214 may function to generate synthetic prescriptions. Synthetic prescriptions may be used to obtain insurance information as if the synthetic prescription was an actual request to fill an electronic prescription. The synthetic prescription engine 214 may generate synthetic prescriptions from electronic prescriptions 122 and/or prescription query requests.

In some embodiments, the information gathering engine 216 may function to gather insurance information 250. For example, the information gathering engine 216 may provide requests (e.g., synthetic prescriptions) to a remote system (e.g., switching system 110 and/or payer system 112) for insurance information, and receive information from remote systems based on the requests. The information gathering engine 216 may auto-reverse the requests once the insurance information is received.

In some embodiments, the information gathering engine 216 may function to gather pharmacy information 124. Pharmacy information may be gathered from pharmacy systems 108 and/or other third party systems. Pharmacy information 124 may be stored locally in pharmacy datastore 208. In some embodiments, the information gathering engine 216 may function to gather promotion information 252. For example, promotion information 252 may be gathered from pharmacy systems and/or other third-party systems.

The payment analysis engine 218 may function to determine patient payment amounts for particular medications. In some embodiments, the payment analysis engine 218 may identify cash-pay amounts, co-pay amounts, and/or promotion discount amounts, and determine a patient payment amount. For example, the payment analysis engine 218 may determine a cash-pay amount based on pharmacy information 124, optionally adjust the cash-pay amount based on any applicable promotion information 252, determine a co-pay amount if the patient is ensured and the medication is covered, and then compare the cash-pay and co-pay amounts. The lowest amount may be the patient payment amount.

The restriction analysis engine 220 may function to identify restrictions associated with an electronic prescription 122. In some embodiments, the restriction analysis engine 220 may identify restrictions based on insurance information 250 and/or patient information 240. For example, the restriction analysis engine 220 may automatically check for restrictions in response to receiving and/or buffering an electronic prescription 122. In some embodiments, restriction analysis engine 220 may determine whether the insurance information 250 and/or patient information 240 is stale. The restriction analysis engine 220 may trigger gathering of current information for some or all stale information.

The interactive routing server engine 222 may function to route electronic prescriptions 122 to a particular pharmacy system 108 based on one or more interactions with a patient. For example, the interactive routing server engine 222 may query a patient regarding a preferred pharmacy, and route the electronic prescription 122 to the associated preferred pharmacy system 108.

In some embodiments, the interactive routing server engine 222 may identify a set of suitable pharmacies that may be capable of fulfilling an electronic prescription 1122, generate a data message including the set of suitable pharmacies, and provide the data message to a user system 104 associated with the patient. The interactive routing server engine 222 may receive a response from the user system 104 including identification of a patient-selected pharmacy, and then the interactive routing server engine 222 may route the electronic prescription 122 to the patient-selected pharmacy.

The prescription query processing engine 224 may function to handle prescription query requests. A prescription query request may include a request to determine a patient payment amount for a particular medication for one or more patients. For example, the prescription query processing engine 224 may receive a prescription query request, cause the information gathering engine 216 to obtain insurance information 250, and cause the payment analysis engine 218 to determine the patient payment amount based on the insurance information. The prescription query processing engine 224 may provide the patient payment amount to one or more remote systems (e.g., user systems 104) in the form of a query response and/or other data message.

The notification engine 226 may function to generate and/or provide alerts, messages, and/or other notifications. For example, notifications may be provided to user systems 104, pharmacy systems 108, provider systems 106, and/or the like. In some embodiments, the notification engine 226 may generate notifications based on prescription status.

The communication engine 228 may function to send requests, transmit and, receive communications, and/or otherwise provide communication with one or a plurality of systems. In some embodiments, the communication engine 228 functions to encrypt and decrypt communications. The communication engine 228 may function to send requests to and receive data from one or more systems through a network or a portion of a network. Depending upon implementation-specified considerations, the communication engine 228 may send requests and receive data through a connection, all or a portion of which may be a wireless connection. The communication engine 228 may request and receive messages, and/or other communications from associated systems. Communications may be stored at least temporarily (e.g., cached and/or persistently) in the interactive routing server system datastore 230.

The interactive routing server system datastore 230 may function to store, at least temporarily, data received from one or more other systems. For example, the interactive routing server system datastore 230 may store messages received by the communication engine 228. Like other datastores described herein, the interactive routing server system datastore 230 may reside local to the interactive routing server system 102, or comprise an associated remote storage system (e.g., a cloud storage system).

In some embodiments, the interactive routing server system datastore 230 temporarily stores insurance information 250 and promotion information 252. In some embodiments, the insurance information 250 and/or promotion information 252 may be stored persistently instead of, or in addition to, temporarily.

Figure 3:
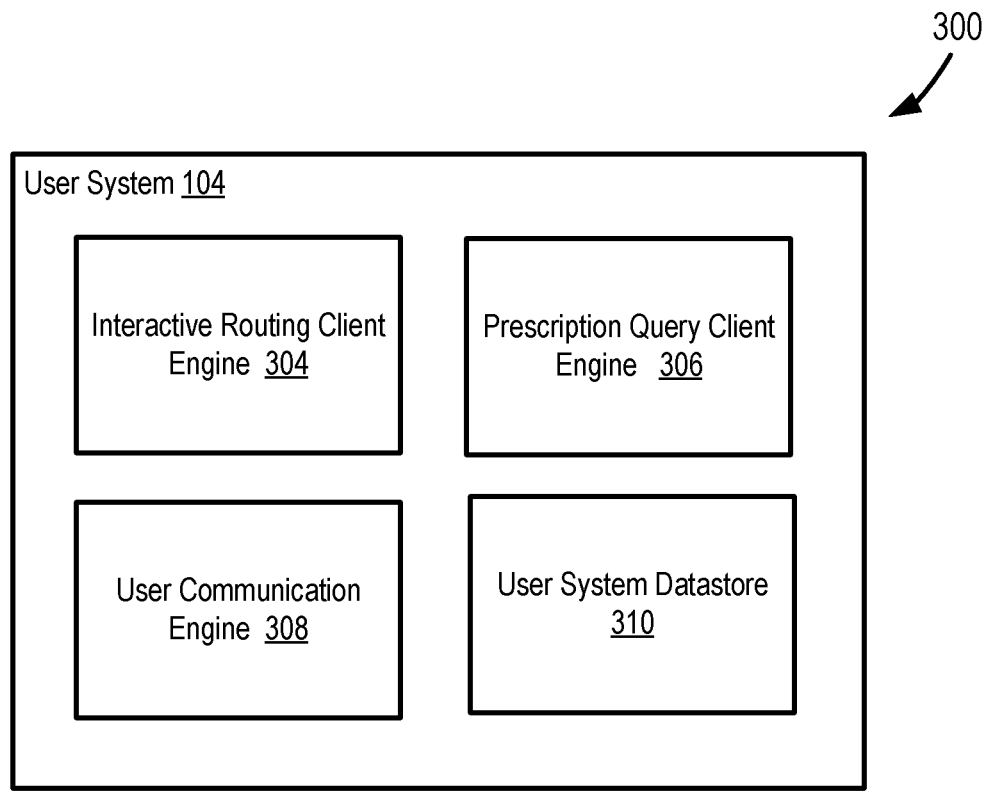
FIG. 3 depicts a diagram of an example of a user system according to some embodiments.

FIG. 3 depicts a diagram 300 of an example of a user system 104 according to some embodiments. In the example of FIG. 3, the user system 104 includes an interactive routing client engine 304, a prescription query client engine 306, a communication engine 308, and a user system datastore 310.

The interactive routing client engine 304 may function to facilitate interactive routing of electronic prescriptions 122. In some embodiments, the interactive routing client engine 304 functions to present a set of suitable pharmacies from which a patient may select a particular pharmacy to receive the electronic prescription 122. The interactive routing client engine 304 may receive input from the patient, and provide the input to one or more remote systems (e.g., interactive routing server system 102).

The prescription query client engine 306 may function receive pharmaceutical information (e.g., name or other identifier) and insurance information (e.g., patient insurance identifier), and generate pharmaceutical queries therefrom. In some embodiments, the prescription query client engine 306 provides a graphical user interface for receiving input and displaying information.

The communication engine 308 may function to send requests, transmit, and receive communications, and/or otherwise provide communication with one or a plurality of systems. In some embodiments, the communication engine 308 functions to encrypt and decrypt communications. The communication engine 308 may function to send requests to and receive data from one or more systems through a network or a portion of a network. Depending upon implementation-specified considerations, the communication engine 308 may send requests and receive data through a connection, all or a portion of which may be a wireless connection. The communication engine 308 may request and receive messages, and/or other communications from associated systems. Communications may be stored at least temporarily (e.g., cached and/or persistently) in the user system datastore 310.

The user system datastore 310 may function to store, at least temporarily, data received from one or more other systems. For example, the interactive routing server system datastore 230 may store messages received by the communication engine 308. Like other datastores described herein, the user system datastore 310 may reside local to the user system 104, or comprise an associated remote storage system (e.g., a cloud storage system).

Figure 4:
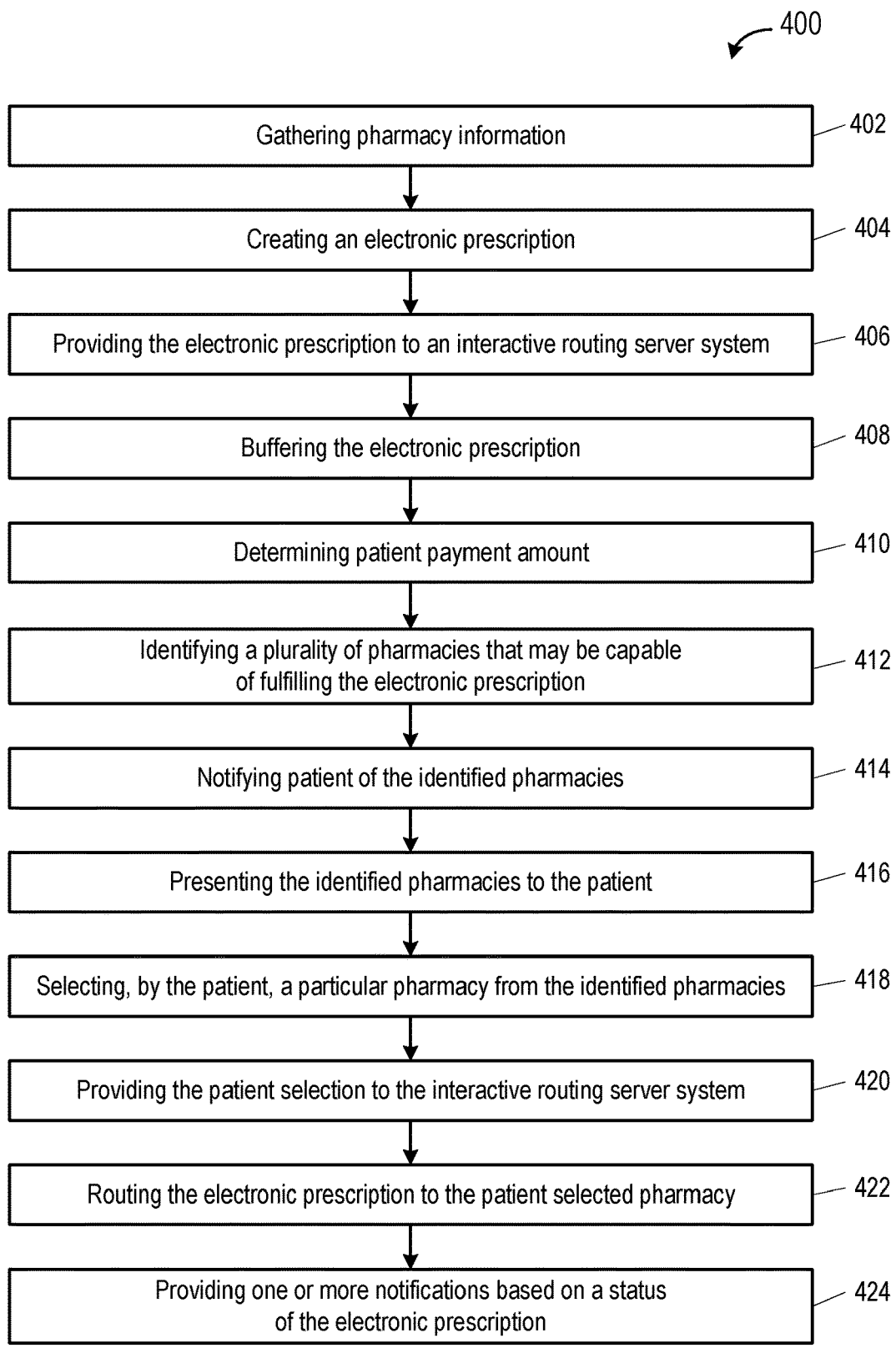
FIG. 4 depicts a flowchart of an example of a method of buffering and interactively routing electronic prescriptions according to some embodiments.

FIG. 4 depicts a flowchart 400 of an example of a method of buffering and interactively routing electronic prescriptions according to some embodiments. In this and other flowcharts, the flowchart illustrates by way of example a sequence of steps. It should be understood the steps may be reorganized for parallel execution, or reordered, as applicable. Moreover, some steps that could have been included may have been removed to avoid providing too much information for the sake of clarity and some steps that were included could be removed, but may have been included for the sake of illustrative clarity.

In step 402, an interactive routing server system (e.g., interactive routing server system 102) gathers pharmacy information (e.g., pharmacy information 124). For example, the interactive routing server system may gather pharmacy information from one or more pharmacy systems (e.g., pharmacy systems 108) and/or third-party services systems. The pharmacy information may include pharmaceutical inventory information, pharmaceutical pricing information, and/or pharmaceutical promotion information. In some embodiments, an information gathering engine (e.g., information gathering engine 216) gathers the pharmacy information. For example, the information gather engine may use one or more server system interface (e.g., server system interface 120) to cooperate with one or more pharmacy system interfaces (e.g., pharmacy system interfaces 130) to gather the pharmacy information.

In some embodiments, the pharmacy information may be stored in one or more datastores (e.g., pharmacy datastore 208). For example, a management engine (e.g., management engine 202) may store the pharmacy information in a local datastore (e.g., pharmacy datastore 208).

In step 404, a provider system (e.g., provider system 106) creates an electronic prescription (e.g., electronic prescription 122). For example, a provider may input pharmaceutical and/or patient information into the provider system and the provider system and/or related system (e.g., a cloud-based system) may create the electronic prescription.

In step 406, the provider system provides the electronic prescription to an interactive routing server system (e.g., interactive routing server system 102). For example, a provider interacting with the provider system may select a pharmacy from a list of available pharmacies. In some embodiments, the selected pharmacy may represent the interactive routing server system (e.g., as opposed to an actual pharmacy), and the provider may or may not be aware that the selected pharmacy is not an actual pharmacy. The provider system may transmit, and/or cause a related system to transmit, the electronic prescription over a communication network (e.g., communication network 114) to the interactive routing server system (e.g., as opposed to routing the electronic prescription to an actual pharmacy for fulfillment).

In step 408, the interactive routing server system buffers the electronic prescription. In some embodiments, a communication engine (e.g., communication engine 228) receives the electronic prescription over the communication network (e.g., from the provider system), and the management engine stores the electronic prescription in a prescription buffer datastore (e.g., prescription buffer datastore 204). For example, the interactive routing server system may store the electronic prescription for a limited amount of time in the prescription buffer datastore (e.g., until it is interactively routed to a particular pharmacy, as discussed further below). In some embodiments, the interactive routing server system may store the electronic prescription persistently (e.g., in interactive routing server system datastore 230).

In step 410, the interactive routing server system determines patient payment amount. An example method of determining patient payment amount is described in FIG. 6.

In step 412, the interactive routing server system identifies a plurality of pharmacies (e.g., pharmacy systems 108) that may be capable of fulfilling the electronic prescription. For example, the interactive routing server system may identify the pharmacies based on patient information (e.g., patient information 240) associated with the patient to whom the electronic prescription was prescribed, and/or based on some or all of the pharmacy information. In some embodiments, an interactive routing server engine (e.g., interactive routing server engine 222) identifies the pharmacies.

In step 414, the interactive routing server system notifies a patient of the plurality of pharmacies based on the patient information. In some embodiments, an interactive routing server engine (e.g., interactive routing server engine 222) may generate an interactive routing request message including the plurality of pharmacies, and the communication engine may provide the interactive routing request message to a user system (e.g., user system 104) associated with the patient based on a phone number of the patient or other patient identifier of the patient.

In step 416, the user system presents the identified pharmacies. In some embodiments, an interactive routing client engine (e.g., interactive routing client engine 304) generates and/or displays a graphical user interface, and presents the identified pharmacies through the graphical user interface. For example, the interactive routing client engine may cooperate with the interactive routing server engine to present the identified pharmacies received by a user communication engine (e.g., user communication engine 308) over the communication network).

In step 418, the patient selects a particular pharmacy from the identified pharmacies. In some embodiments the patients selects the particular pharmacy through a graphical user interface generated by the interactive routing client engine.

In some embodiments, the interactive routing server system selects the particular pharmacy based on one or more rules (e.g., pharmacy selection rules) and/or other criteria (e.g., user defined parameters). For example, the patient may specify preferences and/or hierarchy of pharmacies based on geographical location, patient payment amount, pharmacy inventory, and/or the like, and the interactive routing server system may select the particular pharmacy accordingly.

In step 420, the user system provides the patient selection of the particular pharmacy to the interactive routing server system. In some embodiments, the user communication engine provides the selection to the interactive routing server system over the communication network.

In step 422, the interactive routing server system routes the electronic prescription to the particular pharmacy based on the patient selection. In some embodiments, the interactive routing server engine routes the electronic prescription to the particular pharmacy. For example, the interactive routing server engine may identify a particular pharmacy system (e.g., a particular pharmacy system 108) associated with the particular pharmacy, and cooperate with the communication engine to route the electronic prescription over the communication network to the particular pharmacy system (e.g., using an email address, phone number, fax number, and/or URI associated with the particular pharmacy system).

In step 424, the interactive routing server system provides one or more notifications based on a status of the electronic prescription. For example, the interactive routing server system may notify the provider and/or patient when the electronic prescription has been sent to the particular pharmacy, when the electronic prescription has been received by the particular pharmacy, when the electronic prescription has been filled and/or is ready for pickup. In some embodiments, the interactive routing server system may notify the provider and/or patient of any restrictions (e.g., as described in FIG. 7 and elsewhere herein). In some embodiments, a notification engine (e.g., notification engine 226) generates notifications and cooperates with the communication engine to provide the notifications to the provider and/or patient over the communication network.

Figure 5:
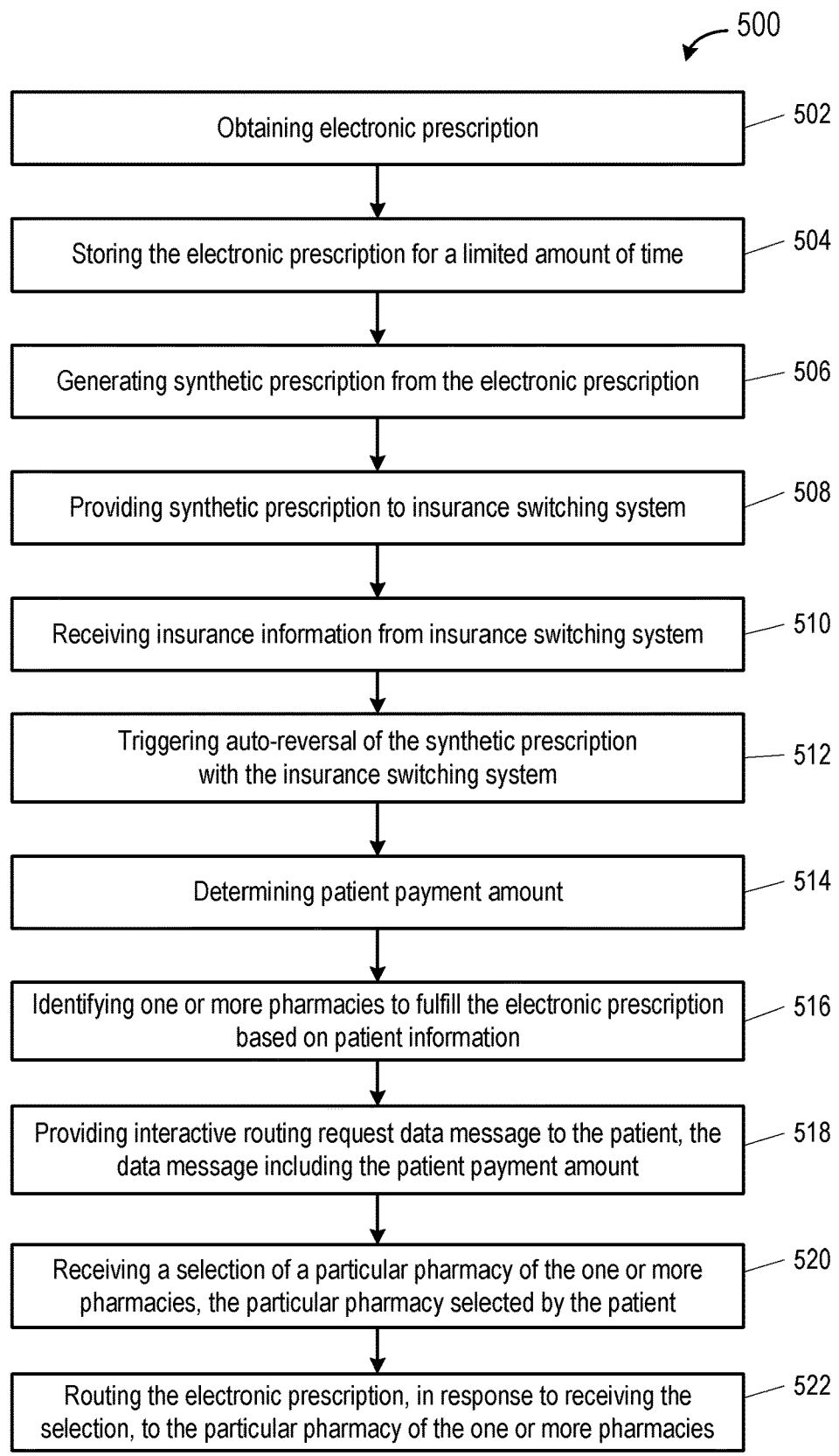
FIG. 5 depicts a flowchart of an example of a method of buffering and interactively routing electronic prescriptions according to some embodiments.

FIG. 5 depicts a flowchart 500 of an example of a method of buffering and interactively routing electronic prescriptions according to some embodiments.

In step 502, an interactive routing server system (e.g., interactive routing server system 102) obtains an electronic prescription (e.g., an electronic prescription 122) over a communication network (e.g., communication network 114), the electronic prescription being associated with a patient and identifying a particular pharmaceutical. In some embodiments, a communication engine (e.g., communication engine 228) obtains the electronic prescription.

In step 504, the interactive routing server system stores the electronic prescription for a limited amount of time. In some embodiments, a buffering engine (e.g., buffering engine 212) stores the electronic prescription in a prescription buffer datastore (e.g., prescription buffer datastore 204).

In step 506, the interactive routing server system generates a synthetic prescription from the electronic prescription. For example, the synthetic prescription may include a patient insurance identifier associated with the patient, and a pharmaceutical identifier of the particular pharmaceutical. In some embodiments, a synthetic prescription engine 214 generates the synthetic prescription.

In step 508, the interactive routing server system provides the synthetic prescription to an insurance switching system (e.g., switching system 110). In some embodiments, the synthetic prescription is capable of being processed by the insurance switching system as if it were an actual request to fulfill the electronic prescription. In some embodiments, an information gathering engine (e.g., information gathering engine 216) cooperates with the communication engine to provide the synthetic prescription to the insurance switching system over the communication network. In some embodiments, the information gathering engine may utilize one or more server system interfaces to cooperate with a switching system interface (e.g., switching system interface 140) to provide the synthetic prescription to the insurance switching system over the communication network.

In step 510, the interactive routing server system receives insurance information (e.g., insurance information 250) of the patient from the insurance switching system based on the synthetic prescription. For example, the insurance information may include whether the patient has insurance coverage, and if the patient has insurance coverage, any insurance coverage information. For example, the insurance coverage information may include co-pay amounts (e.g., co-pay for the particular pharmaceutical), restrictions, and/or the like. In some embodiments, the information gathering engine may utilize one or more server system interfaces to cooperate with the switching system interface to receive the insurance information of the patient over the communication network.

In step 512, the interactive routing server system triggers an auto-reversal of the synthetic prescription with the insurance switching system. For example, the interactive routing server system may send a data message to the insurance switching system that causes the switching system to cancel a request to fulfill the electronic prescription. In some embodiments, the information gathering engine may trigger the auto-reversal.

In step 514, the interactive routing server system determines a patient payment amount associated with the particular pharmaceutical based on the insurance information. For example, the patient payment amount may include a deductible amount, a co-pay amount, a cash-pay amount, and/or a promotion discount amount. In some embodiments, a payment analysis engine (e.g., payment analysis engine 218) determines the patient payment amount.

In step 516, the interactive routing server system identifies one or more pharmacies to fulfill the electronic prescription based on patient information (e.g., patient information 240) of the patient. For example, the patient information may include a predetermined geographic location of the patient, a current geographic location of the patient, and/or one or more predetermined pharmacy selection rules. The patient information may be stored in a patient datastore (e.g., patient datastore 206). In some embodiments, an interactive routing server engine (e.g., interactive routing server engine 222) identifies the one or more pharmacies.

In some embodiments, the interactive routing server system may identify the one or more pharmacies based on the patient payment amount associated with the particular pharmaceutical in addition to, or instead of, the patient information.

In step 518, the interactive routing server system provides an interactive routing request data message to the patient.

The data message may include the patient payment amount associated with the particular pharmaceutical and a request for selection of a particular pharmacy of the one or more pharmacies by the patient. In some embodiments, the interactive routing server engine generates the data message and identifies a destination for the data message (e.g., a phone number or other patient identifier), and the communication engine provides the data message to the identified destination over the communication network.

In step 520, the interactive routing server system receives the selection of the particular pharmacy of the one or more pharmacies from a computing device (e.g., user system 104) associated with the patient. In some embodiments, the interactive routing server engine cooperates with the communication engine to receive the selection over the communication network.

In step 522, the interactive routing server system routes the electronic prescription, in response to receiving the selection from the computing device associated with the patient, to the particular pharmacy of the one or more pharmacies. In some embodiments, the interactive routing server engine uses a server system interface (e.g., server system interface 120) to cooperate with a pharmacy system interface (e.g., pharmacy system interface 130) to route the electronic prescription to the particular pharmacy.

Figure 6:
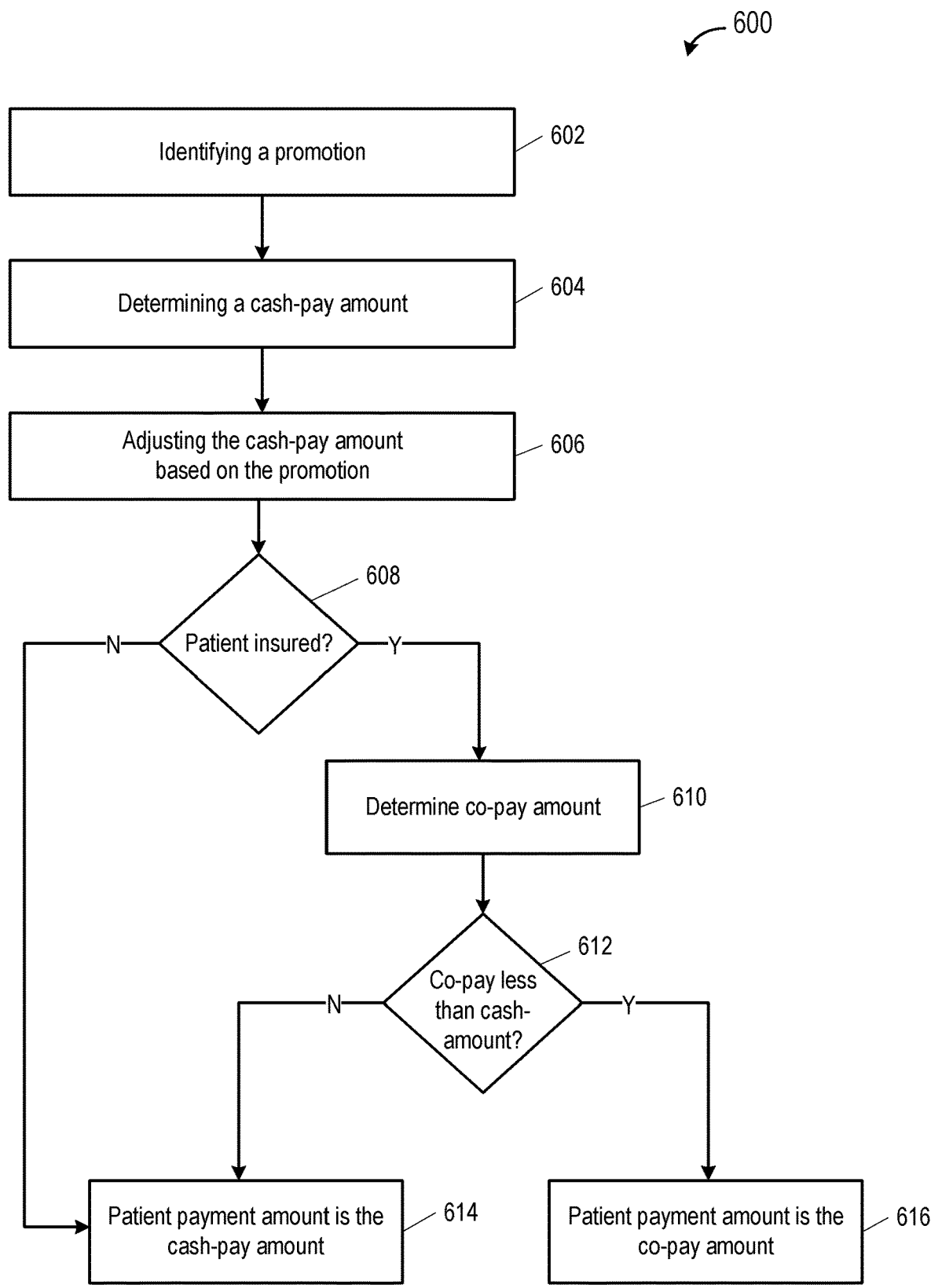
FIG. 6 depicts a flowchart of an example of a method of determining patient payment amount for an electronic prescription according to some embodiments.

FIG. 6 depicts a flowchart 600 of an example of a method of determining patient payment amount for an electronic prescription according to some embodiments.

In step 602, an interactive routing server system (e.g., interactive routing server system 102) identifies a promotion. In some embodiments, an information gathering engine (e.g., information gathering engine 216) identifies the promotion based on patient information (e.g., patient information 240) and/or pharmacy information (e.g., pharmacy information 124). In some embodiments, the information gathering engine may identify promotion information (e.g., promotion information 252) from the promotion.

In step 604, the interactive routing server system determines a cash-pay amount. In some embodiments, a payment analysis engine (e.g., payment analysis engine 218) determines the cash-pay amount. For example, the payment analysis engine may look up the cash-pay amount in the pharmacy information stored in a pharmacy datastore (e.g., pharmacy datastore 208).

In step 606, the interactive routing server system adjusts the cash-pay amount based on the promotion. In some embodiments, the payment analysis engine adjusts the cash-pay amount.

In step 608, the interactive routing server system determines whether patient is insured. In some embodiments, the payment analysis engine determines whether the patient is insured. For example, the information gathering engine may obtain patient insurance information, and the payment analysis engine may determine whether the patient is insured based on the patient insurance information.

In step 610, the interactive routing server system, if the patient is insured, determines a co-pay amount. In some embodiments, the payment analysis engine determines the co-pay amount from the patient insurance information obtained by the interactive routing server system.

In step 612, the interactive routing server system determines whether the co-pay amount is less than the cash-pay amount (and/or vice versa). In some embodiments, the payment analysis engine performs the determination.

In step 614, the interactive routing server system determines the patient payment amount is the cash-pay amount if the co-pay amount is not less than the cash-pay amount. Other comparison conditions may also be used (e.g., not less than or equal to). In some embodiments, the payment analysis engine performs the determination.

In step 616, the interactive routing server system determines the patient payment amount is the co-pay amount if the co-pay amount is less than the cash-pay amount. Other comparison conditions may also be used (e.g., less than or equal to). In some embodiments, the payment analysis engine performs the determination.

Figure 7:
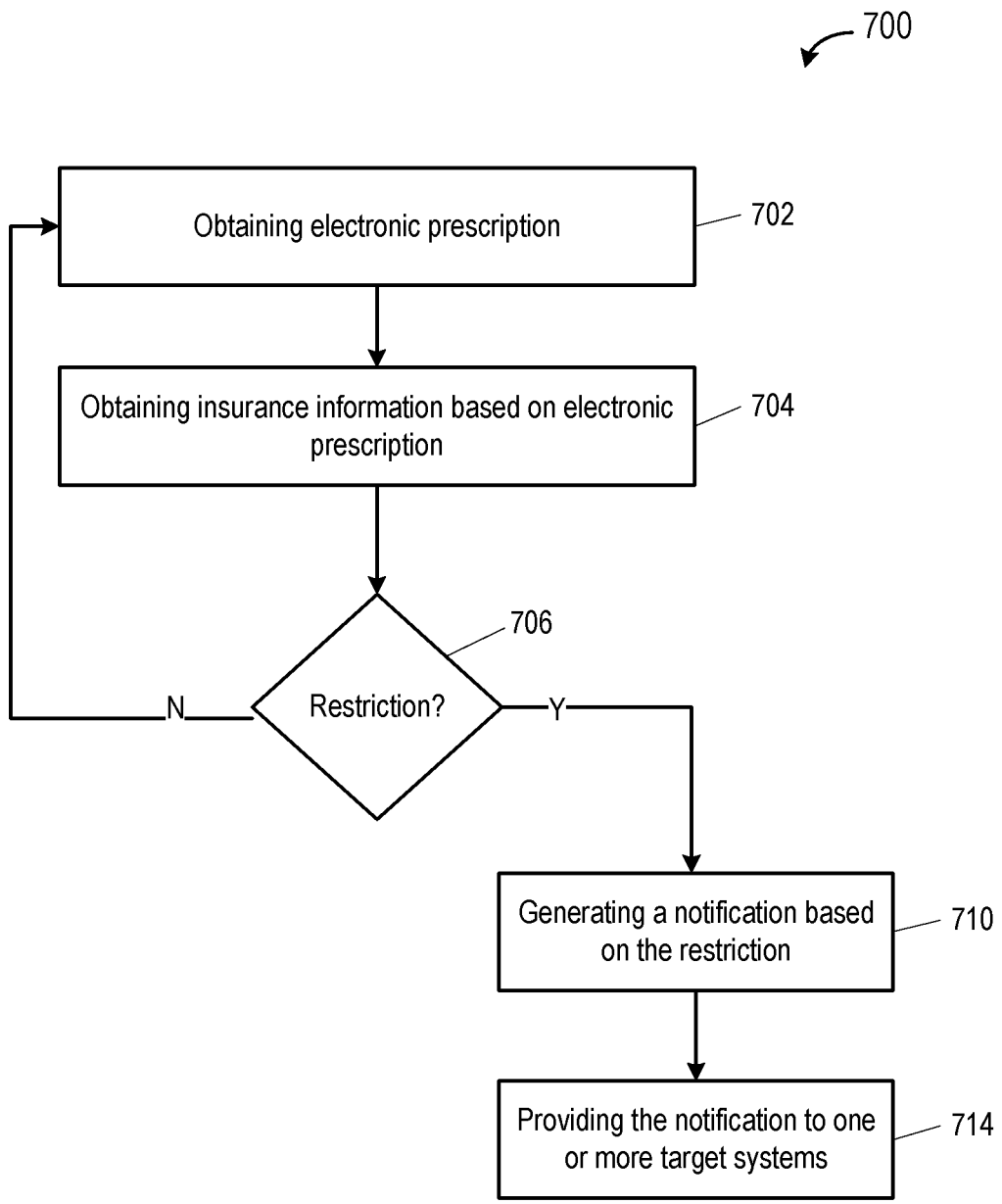
FIG. 7 depicts a flowchart of an example of a method of handling restrictions during interactive routing of electronic prescriptions according to some embodiments.

FIG. 7 depicts a flowchart 700 of an example of a method of handling restrictions during interactive routing of electronic prescriptions according to some embodiments.

In step 702, an interactive routing server system (e.g., interactive routing server system 102) obtains an electronic prescription (e.g., electronic prescription 122). In some embodiments, a communication engine (e.g., communication engine 228) obtains the electronic prescription.

In step 704, the interactive routing server system obtains insurance information (e.g., insurance information 250) based on the electronic prescription. In some embodiments, an information gathering engine (e.g., information gathering engine 216) obtains the insurance information.

In step 706, the interactive routing server system determines whether the insurance information includes one or more restrictions. In some embodiments, a restriction analysis engine (e.g., restriction analysis engine 220) performs the determination.

In step 708, the interactive routing server system generates a notification based on the restriction. In some embodiments, a notification engine (e.g., notification engine 226) generates the notification.

In step 710, the interactive routing server system provides the notification to one or more target systems. For example, the one or more target systems may include a user system (e.g., user system 104) and/or provider system (e.g., provider system 106). In some embodiments, the notification engine cooperates with the communication engine to provide the notification over the communication network to the one or more target systems.

Figure 8:
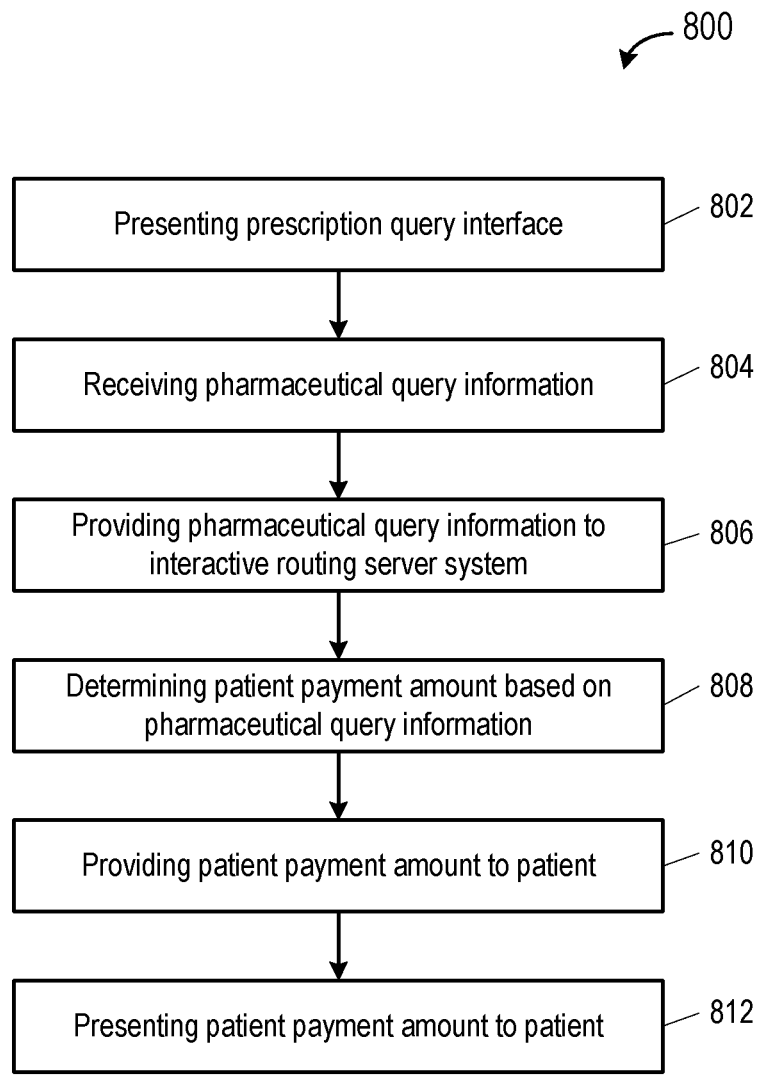
FIG. 8 depicts a flowchart of an example of a method of performing a pharmaceutical query according to some embodiments.

FIG. 8 depicts a flowchart 800 of an example of a method of performing a pharmaceutical query according to some embodiments.

In step 802, a user system (e.g., user system 104) presents a prescription query interface. In some embodiments, a prescription query client engine (e.g., prescription query client engine 306) presents the prescription query interface.

In step 804, the user system receives pharmaceutical query information through the prescription query interface. For example, the pharmaceutical query information may include a pharmaceutical identifier (e.g., pharmaceutical name) and patient insurance information of a patient associated with the user system. In some embodiments, the prescription query client engine receives the information.

In step 806, the user system provides the pharmaceutical query information to an interactive routing server system (e.g., interactive routing server system 102). In some embodiments, the prescription query client engine cooperates with a user communication engine (e.g., user communication engine 308) to provide the pharmaceutical query information the interactive routing server system over a communication network (e.g., communication network 114).

In step 808, the interactive routing server system determines a patient payment amount based on the pharmaceutical query information. An example method of determining patient payment amount is described in FIG. 6.

In step 810, the interactive routing server system provides the patient payment amount to the user system. In some embodiments, the prescription query processing engine cooperates with the communication engine to provide the patient payment to the user system.

In step 812, the user system presents the patient payment information to the patient through the prescription query interface. In some embodiments, the prescription query client engine presents the patient payment information.

Figure 9:
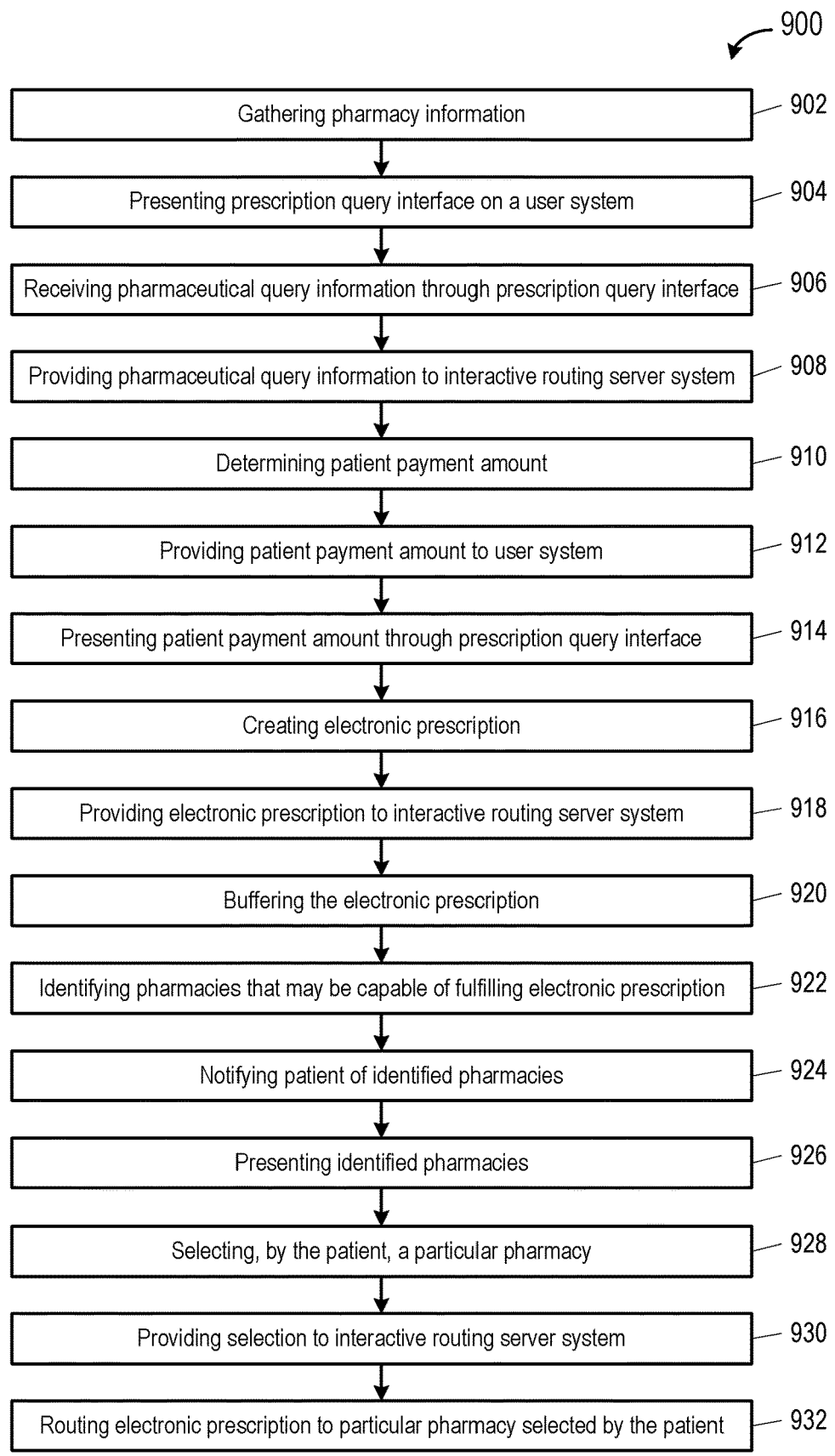
FIG. 9 depicts a flowchart of an example of method of performing a pharmaceutical query and interactively routing electronic prescriptions.

FIG. 9 depicts a flowchart 900 of an example of method of performing a pharmaceutical query and interactively routing electronic prescriptions.

In step 902, an interactive routing server system (e.g., interactive routing server system 102) gathers pharmacy information (e.g., pharmacy information 124). In some embodiments, an information gathering engine (e.g., information gathering engine 216) gathers the pharmacy information, and a management engine (e.g., management engine 202) stores the pharmacy information in a pharmacy datastore (e.g., pharmacy datastore 208).

In step 904, a user system (e.g., user system 104) presents a prescription query interface. In some embodiments, a prescription query client engine (e.g., prescription query client engine 306) presents the prescription query interface.

In step 906, the user system receives pharmaceutical query information through the prescription query interface. In some embodiments, the prescription query client engine receives the information.

In step 908, the user system provides the pharmaceutical query information to the interactive routing server system. In some embodiments, the prescription query client engine cooperates with a user communication engine (e.g., user communication engine 308) to provide the pharmaceutical query information to the interactive routing server system over a communication network (e.g., communication network 114).

In step 910, the interactive routing server system determines a patient payment amount based on the pharmaceutical query information. In some embodiments, a prescription query processing engine (e.g., prescription query processing engine 224) determines the patient payment amount.

In step 912, the interactive routing server system provides the patient payment amount to the user system. In some embodiments, the prescription query processing engine cooperates with a communication engine (e.g., communication engine 228) to provide the patient payment amount to the user system over the communication network.

In step 914, the user system presents the patient payment information through the prescription query interface. In some embodiments, the prescription query processing engine cooperates with the communication engine to provide the patient payment to the user system.

In step 916, a provider system (e.g., provider system 106) creates an electronic prescription (e.g., electronic prescription 122). For example, a provider may input pharmaceutical and/or patient information into the provider system and the provider system and/or related system (e.g., a cloud-based system) may create the electronic prescription.

In step 918, the provider system provides the electronic prescription to an interactive routing server system (e.g., interactive routing server system 102). For example, a provider interacting with the provider system may select a pharmacy from a list of available pharmacies, and the selected pharmacy actually represents the interactive routing server system (e.g., as opposed to being an actual pharmacy). The provider system may transmit, and/or cause a related system to transmit, the electronic prescription over a communication network (e.g., communication network 114) to the interactive routing server system (e.g., as opposed to routing the electronic prescription to an actual pharmacy for fulfillment).

In step 920, the interactive routing server system buffers the electronic prescription. In some embodiments, a communication engine (e.g., communication engine 228) receives the electronic prescription over the communication network (e.g., from the provider system), and the management engine stores the electronic prescription in a prescription buffer datastore (e.g., prescription buffer datastore 204). For example, the interactive routing server system nay store the electronic prescription for a limited amount of time in the prescription buffer datastore (e.g., until it is interactively routed to a particular pharmacy, as discussed further below). In some embodiments, the interactive routing server system may store the electronic prescription persistently (e.g., in interactive routing server system datastore 230).

In step 922, the interactive routing server system identifies a plurality of pharmacies that may be capable of fulfilling the prescription. For example, the interactive routing server system may identify the pharmacies based on patient information associated with the patient of to whom the electronic prescription was prescribed, and/or based on some or all of the pharmacy information. In some embodiments, an interactive routing server engine (e.g., interactive routing server engine 222) identifies the pharmacies.

In step 924, the interactive routing server system notifies a patient of the plurality of pharmacies based on the patient information. In some embodiments, the interactive routing server engine notifies the patient.

In step 926, the user system presents the identified pharmacies. In some embodiments, an interactive routing client engine (e.g., interactive routing client engine 304) presents the identified pharmacies. For example, the interactive routing client engine may cooperate with the interactive routing server engine to present the identified pharmacies received by a user communication engine (e.g., user communication engine 308) over the communication network.

In step 928, the patient selects a particular pharmacy from the identified pharmacies. In some embodiments the patients selects the particular pharmacy through a graphical user interface generated by the interactive routing client engine.

In step 930, the user system provides the selection of the particular pharmacy to the interactive routing server system. In some embodiments, the user communication engine provides the selection to the interactive routing server system over the communication network.

In step 932, the interactive routing server system routes the electronic prescription to the particular pharmacy in response to receiving the selection of the particular pharmacy. In some embodiments, the interactive routing server engine routes the electronic prescription to the particular pharmacy.

Figure 10:
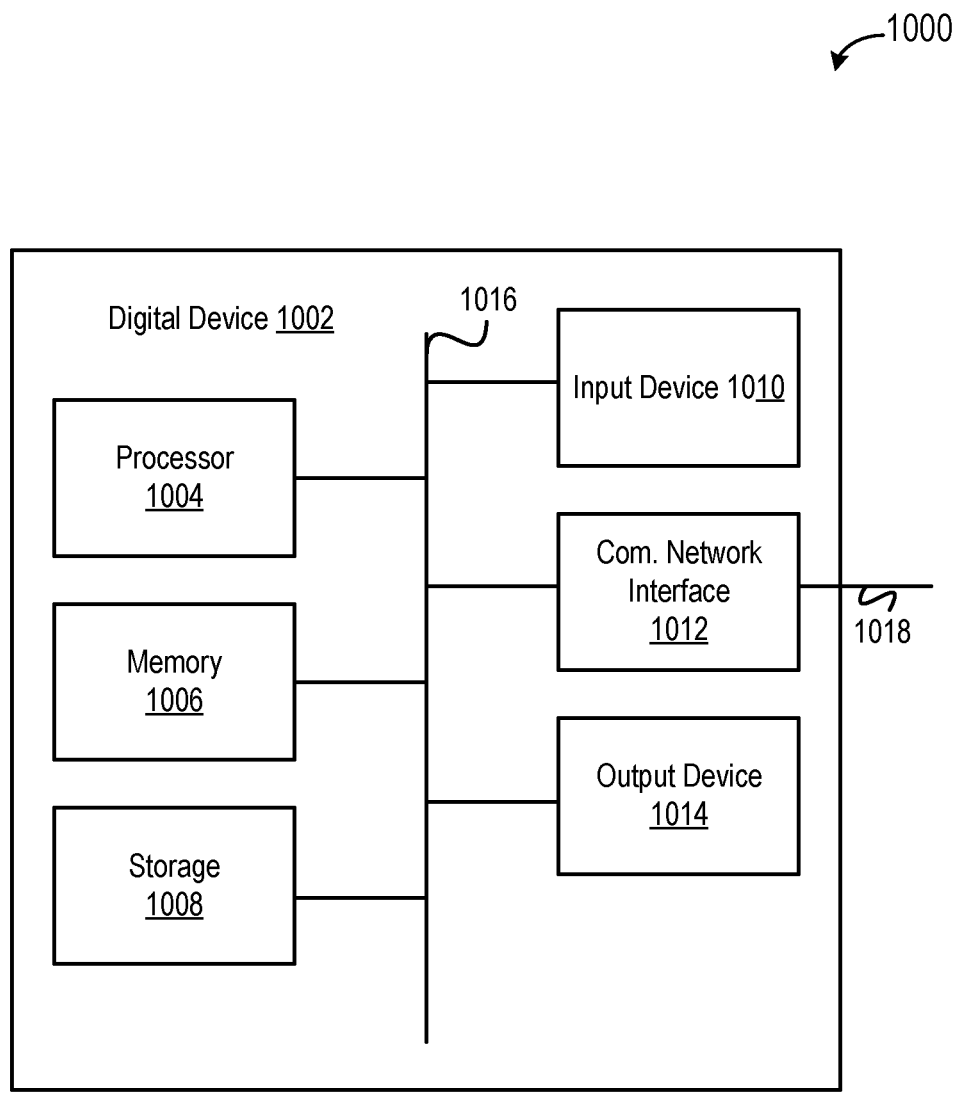
FIG. 10 is a diagram of an example computer system for implementing the features disclosed herein.

FIG. 10 depicts a diagram 1000 of an example of a computing device 1002. Any of the systems 102-112 and the communication network 114 may comprise an instance of one or more computing devices 1002. The computing device 1002 comprises a processor 1004, memory 1006, storage 1008, an input device 1010, a communication network interface 1012, and an output device 1014 communicatively coupled to a communication channel 1016. The processor 1004 is configured to execute executable instructions (e.g., programs). In some embodiments, the processor 1004 comprises circuitry or any processor capable of processing the executable instructions.

The memory 1006 stores data. Some examples of memory 1006 include storage devices, such as RAM, ROM, RAM cache, virtual memory, etc. In various embodiments, working data is stored within the memory 1006. The data within the memory 1006 may be cleared or ultimately transferred to the storage 1008.

The storage 1008 includes any storage configured to retrieve and store data. Some examples of the storage 1008 include flash drives, hard drives, optical drives, cloud storage, and/or magnetic tape. Each of the memory system 1006 and the storage system 1008 comprises a computer-readable medium, which stores instructions or programs executable by processor 1004.

The input device 1010 is any device that inputs data (e.g., mouse and keyboard). The output device 1014 outputs data (e.g., a speaker or display). It will be appreciated that the storage 1008, input device 1010, and output device 1014 may be optional. For example, the routers/switchers may comprise the processor 1004 and memory 1006 as well as a device to receive and output data (e.g., the communication network interface 1012 and/or the output device 1014).

The communication network interface 1012 may be coupled to a network (e.g., network 114) via the link 1018. The communication network interface 1012 may support communication over an Ethernet connection, a serial connection, a parallel connection, and/or an ATA connection. The communication network interface 1012 may also support wireless communication (e.g., 802.11 a/b/g/n, WiMax, LTE, WiFi). It will be apparent that the communication network interface 1012 may support many wired and wireless standards.

It will be appreciated that the hardware elements of the computing device 1002 are not limited to those depicted in FIG. 10. A computing device 1002 may comprise more or less hardware, software and/or firmware components than those depicted (e.g., drivers, operating systems, touch screens, biometric analyzers, and/or the like). Further, hardware elements may share functionality and still be within various embodiments described herein. In one example, encoding and/or decoding may be performed by the processor 1004 and/or a co-processor located on a GPU (e.g., NVidia).

It will be appreciated that an "engine," "system," "datastore," and/or "database" may comprise software, hardware, firmware, and/or circuitry. In one example, one or more software programs comprising instructions capable of being executable by a processor may perform one or more of the functions of the engines, datastores, databases, or systems described herein. In another example, circuitry may perform the same or similar functions. Alternative embodiments may comprise more, less, or functionally equivalent engines, systems, datastores, or databases, and still be within the scope of present embodiments. For example, the functionality of the various systems, engines, datastores, and/or databases may be combined or divided differently. The datastore or database may include cloud storage. It will further be appreciated that the term "or," as used herein, may be construed in either an inclusive or exclusive sense. Moreover, plural instances may be provided for resources, operations, or structures described herein as a single instance.

The datastores described herein may be any suitable structure (e.g., an active database, a relational database, a self-referential database, a table, a matrix, an array, a flat file, a documented-oriented storage system, a non-relational No-SQL system, and the like), and may be cloud-based or otherwise.

The systems, methods, engines, datastores, and/or databases described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The present invention(s) are described above with reference to example embodiments. It will be apparent to those skilled in the art that various modifications may be made and other embodiments may be used without departing from the broader scope of the present invention(s). Therefore, these and other variations upon the example embodiments are intended to be covered by the present invention(s).

The invention claimed is:

1. A method comprising:
obtaining, by an interactive routing server system from a plurality of different provider systems, a plurality of electronic prescriptions over a communication network, the plurality of electronic prescriptions being associated with a plurality of patients, a plurality of providers, and a plurality of pharmaceuticals, the interactive routing server system providing an interface to the plurality of different provider systems to appear as an actual pharmacy;
temporarily storing, by the interactive routing server system, the plurality of electronic prescriptions in buffer storage until one of a set of one or more trigger conditions occurs, the set of one or more trigger conditions including fulfillment of a respective prescription and including a time limit;
selecting, by the interactive routing server system, a particular electronic prescription from the plurality of electronic prescriptions, the particular electronic prescription being associated with a particular patient and a particular pharmaceutical;

generating, by the interactive routing server system, a plurality of synthetic prescription requests based on the particular electronic prescription, the plurality of synthetic prescription requests being associated with a plurality of different pharmacies;

providing, by the interactive routing server system, the plurality of synthetic prescription requests to an insurance switching system, each synthetic prescription request appearing to the insurance switching system as an actual claim for the particular pharmaceutical by the particular patient at a respective different pharmacy of the plurality of different pharmacies, the interactive routing server system using an application program interface associated with the insurance switching system, the plurality of different pharmacies being determined based on geographic proximity to the particular patient, data identifying prior pharmacies selected by the particular patient, and/or data identifying mail-order pharmacies available to the particular patient;

receiving, by the interactive routing server system, insurance coverage information of the particular patient from the insurance switching system based on each of the plurality of synthetic prescription requests using the application program interface associated with the insurance switching system;

after receiving the insurance coverage information of the particular patient from the insurance switching system based on each of the plurality of synthetic prescription requests, triggering, by the interactive routing server system, an auto-reversal of each of the plurality of synthetic prescription requests with the insurance switching system using the application program interface associated with the insurance switching system;

determining, by the interactive routing server system, a plurality of patient payment amount options associated with the particular pharmaceutical based on the insurance coverage information;

identifying, by the interactive routing server system, one or more particular pharmacies of the plurality of different pharmacies to fulfill the particular electronic prescription;

providing, by the interactive routing server system, fulfillment information to a computing device associated with the particular patient for presentation in a graphical user interface, the fulfillment information including one or more patient payment amount options associated with the particular pharmaceutical and a request for selection of a particular pharmacy of the one or more particular pharmacies and a particular patient payment amount option of the one or more patient payment amount options;

receiving, by the interactive routing server system, a selection of the particular pharmacy of the one or more particular pharmacies and the selection of the particular patient payment amount option of the one or more patient payment amount options from the computing device associated with the user, the selection being made through the graphical user interface, the graphical user interface identifying at least (i) the one or more particular pharmacies that are capable of fulfilling the particular electronic prescription and (ii) the one or more patient payment amount options associated therewith;

routing, by the interactive routing server system in response to receiving the selection from the computing device, the particular electronic prescription to the particular pharmacy of the one or more particular pharmacies for the fulfillment; and after the fulfillment of the particular electronic prescription or after the time limit, deleting the particular electronic prescription from the buffer storage.

2. The method of claim 1, wherein each synthetic prescription request includes a patient insurance identifier associated with the particular patient, and an identifier of the particular pharmaceutical.

3. The method of claim 1, wherein the insurance coverage information of the particular patient includes whether the particular patient has insurance coverage.

4. The method of claim 1, wherein each patient payment amount option reflects a patient payment amount that includes any of a deductible amount, co-pay amount, cash-pay amount, and promotion discount amount.

5. The method of claim 1, wherein the patient information includes a patient identifier and any of a predetermined geographic location of the particular patient, a current geographic location of the particular patient, and one or more predetermined pharmacy selection rules.

6. The method of claim 1, further comprising gathering pharmacy information from the plurality of different pharmacies, the pharmacy information including any of pharmaceutical inventory information, pharmaceutical pricing information, and pharmaceutical promotion information.

7. The method of claim 6, wherein the one or more pharmacies are identified to fulfill the particular electronic prescription based on the pharmacy information.

8. The method of claim 1, wherein the particular electronic prescription is obtained from a provider system associated with a particular provider prescribing the particular electronic prescription.

9. The method of claim 1, further comprising providing a fulfillment notification to the computing device in response to fulfillment of the particular electronic prescription by the particular pharmacy of the one or more particular pharmacies.

10. An interactive routing server system comprising:
one or more processors; and
memory storing instructions that, when executed by the one or more processors, cause the interactive routing server system to perform:
obtaining from a plurality of different provider systems a plurality of electronic prescriptions over a communication network, the plurality of electronic prescriptions being associated with a plurality of patients, a plurality of providers, and a plurality of pharmaceuticals, the interactive routing server system providing an interface to the plurality of different provider systems to appear as an actual pharmacy;
temporarily storing the plurality of electronic prescriptions in buffer storage until one of a set of one or more trigger conditions occurs, the set of one or more trigger conditions including fulfillment of a respective prescription and including a time limit;
selecting a particular electronic prescription from the plurality of electronic prescriptions, the particular electronic prescription being associated with a particular patient and a particular pharmaceutical;
generating a plurality of synthetic prescription requests based on the particular electronic prescription, the plurality of synthetic prescription requests being associated with a plurality of different pharmacies;
providing the plurality of synthetic prescription requests to an insurance switching system, each synthetic prescription request appearing to the insurance switching system as an actual claim for the particular pharmaceutical by the particular patient at a respective different pharmacy of the plurality of different pharmacies, the interactive routing server system using an application program interface associated with the insurance switching system, the plurality of different pharmacies being determined based on geographic proximity to the particular patient, data identifying prior pharmacies selected by the particular patient, and/or data identifying mail-order pharmacies available to the particular patient;

receiving insurance coverage information of the particular patient from the insurance switching system based on each of the plurality of synthetic prescription requests using the application program interface associated with the insurance switching system;

after receiving the insurance coverage information of the particular patient from the insurance switching system based on each of the plurality of synthetic prescription requests, triggering an auto-reversal of each of the plurality of synthetic prescription requests with the insurance switching system using the application program interface associated with the insurance switching system;

determining a plurality of patient payment amount options associated with the particular pharmaceutical based on the insurance coverage information;

identifying one or more particular pharmacies of the plurality of different pharmacies to fulfill the particular electronic prescription;

providing fulfillment information to a computing device associated with the particular patient for presentation in a graphical user interface, the fulfillment information including one or more patient payment amount options associated with the particular pharmaceutical and a request for selection of a particular pharmacy of the one or more particular pharmacies and a particular patient payment amount option of the one or more patient payment amount options;

receiving a selection of the particular pharmacy of the one or more particular pharmacies and the selection of the particular patient payment amount option of the one or more patient payment amount options from the computing device associated with the user, the selection being made through the graphical user interface associated with the computing device, the graphical user interface identifying at least (i) the one or more particular pharmacies that are capable of fulfilling the particular electronic prescription and (ii) the one or more patient payment amount options associated therewith;

routing, in response to receiving the selection from the computing device, the particular electronic prescription to the particular pharmacy of the one or more particular pharmacies for the fulfillment; and after the fulfillment of the particular electronic prescription or after the time limit, deleting the particular electronic prescription from the buffer storage.

11. The system of claim 10, wherein each synthetic prescription request includes a patient insurance identifier associated with the particular patient, and an identifier of the particular pharmaceutical.

12. The system of claim 10, wherein the insurance coverage information of the particular patient includes whether the particular patient has insurance coverage.

13. The system of claim 10, wherein each patient payment amount option reflects a patient payment amount that includes any of a deductible amount, co-pay amount, cash-pay amount, and promotion discount amount.

14. The system of claim 10, wherein the patient information includes a patient identifier and any of a predetermined geographic location of the particular patient, a current geographic location of the particular patient, and one or more predetermined pharmacy selection rules.

15. The system of claim 10, wherein the instructions further cause the system to perform:
gathering pharmacy information from the plurality of different pharmacies, the pharmacy information including any of pharmaceutical inventory information, pharmaceutical pricing information, and pharmaceutical promotion information.

16. The system of claim 15, wherein the identifying the one or more pharmacies to fulfill the particular electronic prescription comprises identifying the one or more pharmacies to fulfill the particular electronic prescription based on the pharmacy information.

17. The system of claim 10, wherein the electronic prescription is obtained from a provider system associated with a particular provider prescribing the particular electronic prescription.

18. The system of claim 10, wherein the instructions further cause the system to perform:
providing a fulfillment notification to the computing device in response to fulfillment of the particular electronic prescription by the particular pharmacy of the one or more particular pharmacies.

19. A non-transitory computer readable medium comprising instructions that, when executed, cause one or more processors to perform:
obtaining from a plurality of different provider systems a plurality of electronic prescriptions over a communication network, the plurality of electronic prescriptions being associated with a plurality of patients, a plurality of providers, and a plurality of pharmaceuticals, the interactive routing server system providing an interface to the plurality of different provider systems to appear as an actual pharmacy;

temporarily storing the plurality of electronic prescriptions in buffer storage until one of a set of one or more trigger conditions occurs, the set of one or more trigger conditions including fulfillment of a respective prescription and including a time limit;

selecting a particular electronic prescription from the plurality of electronic prescriptions, the particular electronic prescription being associated with a particular patient and a particular pharmaceutical;

generating a plurality of synthetic prescription requests based on the particular electronic prescription, the plurality of synthetic prescription requests being associated with a plurality of different pharmacies;

providing the plurality of synthetic prescription requests to an insurance switching system, each synthetic prescription request appearing to the insurance switching system as an actual claim for the particular pharmaceutical by the particular patient at a respective different pharmacy of the plurality of different pharmacies, the interactive routing server system using an application program interface associated with the insurance switching system, the plurality of different set of respective pharmacies being determined based on geographic proximity to the particular patient, data identifying prior pharmacies selected by the particular patient, and/or data identifying mail-order pharmacies available to the particular patient;

receiving insurance coverage information of the particular patient from the insurance switching system based on each of the plurality of synthetic prescription requests using the application program interface associated with the insurance switching system;

after receiving the insurance coverage information of the particular patient from the insurance switching system based on each of the plurality of synthetic prescription requests, triggering an auto-reversal of each of the plurality of synthetic prescription requests with the insurance switching system using the application program interface associated with the insurance switching system;

determining a plurality of patient payment amount options associated with the particular pharmaceutical based on the insurance coverage information;

identifying one or more particular pharmacies of the plurality of different pharmacies to fulfill the particular electronic prescription;

providing fulfillment information to a computing device associated with the particular patient for presentation in a graphical user interface, the fulfillment information including one or more patient payment amount options associated with the particular pharmaceutical and a request for selection of a particular pharmacy of the one or more particular pharmacies and a particular patient payment amount option of the one or more patient payment amount options;

receiving a selection of the particular pharmacy of the one or more particular pharmacies and the selection of the particular patient payment amount option of the one or more patient payment amount options from the computing device associated with the user, the selection being made through the graphical user interface, the graphical user interface identifying at least (i) the one or more particular pharmacies that are capable of fulfilling the particular electronic prescription and (ii) the one or more patient payment amount options associated therewith;

routing, in response to receiving the selection from the computing device, the particular electronic prescription to the particular pharmacy of the one or more particular pharmacies for the fulfillment; and after the fulfillment of the particular electronic prescription or after the time limit, deleting the particular electronic prescription from the buffer storage.

* * * * *